United States Patent [19]

Mitchell et al.

[11] Patent Number: 5,710,283
[45] Date of Patent: Jan. 20, 1998

[54] PREPARATION OF CHIRAL PYRROLIDINONE DERIVATIVES

[75] Inventors: Glynn Mitchell, Cookham; Shaheen Khatoon Vohra, Woodley, both of United Kingdom

[73] Assignee: Zeneca Limited, London, England

[21] Appl. No.: 749,350

[22] Filed: Nov. 21, 1996

[30] Foreign Application Priority Data

Nov. 30, 1995 [GB] United Kingdom .................. 9524526

[51] Int. Cl.[6] ...................... C07D 207/20; C07D 207/50
[52] U.S. Cl. ............................................. 548/530
[58] Field of Search .................................... 548/530

[56] References Cited

FOREIGN PATENT DOCUMENTS

| 94 13652A | 6/1994 | WIPO . |
| 95 33719A | 12/1995 | WIPO . |
| 96 35677A | 11/1996 | WIPO . |

OTHER PUBLICATIONS

Funaki, I. et al., "Synthesis of 3-Aminopyrrolidin-2-ones by an Intramolecular reaction of Aziridinecarboxyamides", *Tetrahedron* (1996), 52 (29) 9909–9924.

Deok-Chan et al., "Stereoselectivity in the Condensation Reactions between Malate Enolate and Imines to 2-Pyrrolidinone Derivatives", *Tetrahedron Letters* (1995), 36(46), 8445–8, 13 Nov. 1995.

*Primary Examiner*—Jose G. Dees
*Assistant Examiner*—Jane C. Osweki
*Attorney, Agent, or Firm*—Joseph R. Snyder; Marian T. Thomson

[57] ABSTRACT

A process for preparing a compound of formula IIa or IIb:

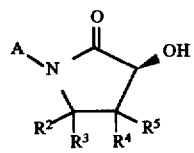

IIa

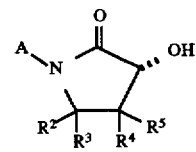

IIb wherein $R^2$, $R^3$, $R^4$ and $R^5$ independently represent hydrogen or $C_1$–$C_4$ alkyl; and A is an optionally substituted aromatic or heteroaromatic ring system; the process comprising the steps of:
(a) reacting a racemic mixture of a compound of formula II:

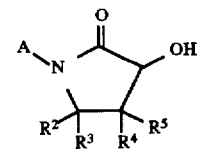

II wherein $R^2$, $R^3$, $R^4$, $R^5$ and A are as defined for formulae IIa and IIb; with a sterically hindered chiral esterifying agent to form enantiomers of formulae IIIa and IIIb:

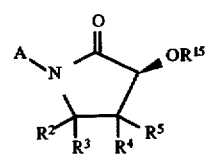

IIIa

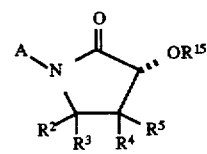

IIIb wherein $R^2$, $R^3$, $R^4$, $R^5$ and A are as defined for formulae IIa and IIb and $R^{15}$ is a chiral sterically hindered residue;
b) separating the diastereoisomers of formulae IIIa and IIIb; and
(c) converting the diastereoisomers of formulae IIIa and IIIb separately to compounds of formulae IIa and IIb respectively by acid or base hydrolysis. If required, the unwanted enantiomer of formula IIa or IIb may be inverted to give the preferred isomer.

10 Claims, No Drawings

PREPARATION OF CHIRAL PYRROLIDINONE DERIVATIVES

The present invention relates to a process for the preparation of chiral compounds which are active as herbicides. In particular, the invention relates to the preparation of chiral pyrrolidinone derivatives.

Pyrrolidinone compounds which are active as herbicides are known from, for example, WO 94/13652 and WO 95/33719 (published after the priority date of the present application). These documents disclose compounds of formula I:

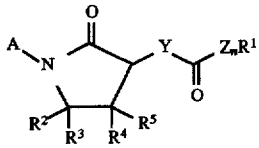

wherein Z is O, S or $NR^6$;
$R^2$, $R^3$, $R^4$, $R^5$ and $R^6$ independently represent hydrogen or $C_1$–$C_4$ alkyl;
n is 0 or 1;
Y is O, S or $NR^7$;
$R^7$ is H, OH, CHO or $NR^{17}R^{18}$, or $C_1$–$C_{10}$ hydrocarbyl or $O(C_1$–$C_{10}$ hydrocarbyl) either of which may be substituted with up to two substituents chosen from $OR^{17}$, $COR^{17}$, $COOR^{17}$, $OCOR^{17}$, CN, halogen, $S(O)_pR^{17}$, $NR^{17}R^{18}$, $NO_2$, $NR^{17}COR^{18}$, $NR^{17}CONR^{18}R^{19}$, $CONR^{17}R^{18}$ and heterocyclyl;
$R^{17}$, $R^{18}$ and $R^{19}$ independently represent hydrogen, $C_1$–$C_6$ hydrocarbyl or $C_1$–$C_6$ halohydrocarbyl;
p is 0, 1 or 2;
alternatively:
when Y is $NR^7$ and either Z is $NR^6$ or n is 0, $R^7$ and the substituents of Z or $R^1$ may together form a bridge represented by the formula $—Q^1—Q^2—$ or $—Q^1—Q^2—Q^3—$, where $Q^1$, $Q^2$ and $Q^3$ independently represent $CR^{13}R^{14}$, $=CR^{13}$, CO, $NR^{16}$, =N, O or S;
$R^{13}$ and $R^{14}$ independently represent hydrogen, $C_1$–$C_4$ alkyl, OH or halogen;
$R^{16}$ represents hydrogen or $C_1$–$C_4$ alkyl;
$R^1$ is hydrogen, or $C_1$–$C_{10}$ hydrocarbyl or heterocyclyl having 3 to 8 ring atoms either of which may optionally be substituted with halogen, hydroxy, $SO_2NR^aR^b$ (where $R^a$ and $R^b$ independently represent hydrogen or $C_1$–$C_6$ alkyl), $SiR^c_3$ (where each $R^c$ is independently $C_1$–$C_4$ alkyl or phenyl), cyano, nitro, amino, mono- and dialkylamino (in which the alkyl groups have from 1 to 6 or more carbon atoms), acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide (in which the groups attached to the N atom may be hydrogen or optionally substituted $C_1$–$C_{10}$ hydrocarbyl), alkoxycarbonyl (wherein the alkoxy group may have from 1 to 6 or more carbon atoms) or aryl;

A is an aromatic or heteroaromatic ring system optionally substituted with one or more substituents selected from halogen, $C_1$–$C_{10}$ hydrocarbyl, $O(C_1$–$C_{10}$ hydrocarbyl), $S(O)_p$ ($C_1$–$C_{10}$ hydrocarbyl), cyano, nitro, SCN, $SiR^c_3$ (where each $R^c$ is independently $C_1$–$C_4$ alkyl or phenyl), $COR^8$, $CR^8NOR^9$, NHOH, $ONR^8R^9$, $SF_5$, $COOR^8$, $SO_2NR^8R^9$, $OR^{10}$ and $NR^{11}R^{12}$; and in which any ring nitrogen atom may be quaternised or oxidised;
alternatively, any two substituents of the group A may combine to form a fused 5- or 6-membered saturated or partially saturated carbocyclic or heterocyclic ring in which any carbon or quaternised nitrogen atom may be substituted with any of the groups mentioned above for A or in which a ring carbon atom may be oxidised;
$R^8$ and $R^9$ independently represent hydrogen or $C_1$–$C_{10}$ hydrocarbyl;
$R^{10}$ is hydrogen, $C_1$–$C_{10}$ hydrocarbyl, $SO_2(C_1$–$C_{10}$ hydrocarbyl), CHO, $CO(C_1$–$C_{10}$ hydrocarbyl), COO ($C_1$–$C_{10}$ hydrocarbyl) or $CONR^8R^9$;
$R^{11}$ and $R^{12}$ independently represent hydrogen, $C_1$–$C_{10}$ hydrocarbyl, $O(C_1$–$C_{10}$ hydrocarbyl), $SO_2(C_1$–$C_{10}$ hydrocarbyl), CHO, $CO(C_1$–$C_{10}$ hydrocarbyl), COO ($C_1$–$C_{10}$ hydrocarbyl) or $CONR^8R^9$;
any of the hydrocarbyl groups within the group A may optionally be substituted with halogen, hydroxy, $SO_2NR^aR^b$ (where $R^a$ and $R^b$ independently represent hydrogen or $C_1$–$C_6$ alkyl), cyano, nitro, amino, mono- and dialkylamino (in which the alkyl groups have from 1 to 6 or more carbon atoms), acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide (in which the groups attached to the N atom may be hydrogen or $C_1$–$C_{10}$ hydrocarbyl optionally substituted with halogen), alkoxycarbonyl (wherein the alkoxy group may have from 1 to 6 or more carbon atom) or aryl.

The expression "$C_1$–$C_{10}$ hydrocarbyl" in the foregoing definitions, whether the expression is used on its own or as part of a larger radical such as, for example, $C_1$–$C_{10}$ hydrocarbyloxy, is intended to include hydrocarbyl radicals of up to ten carbon atoms. Subclasses of such hydrocarbyl radicals include radicals with up to four or up to six carbon atoms. The expression "hydrocarbyl" is intended to include within its scope aliphatic, alicyclic, and aromatic hydrocarbyl groups and combinations thereof. It thus includes, for example, alkyl, alkenyl and alkynyl radicals, cyclopropyl, cyclopropylmethyl, cyclobutyl, cyclopentyl and cyclohexyl radicals, the adamantyl radical and the phenyl radical. The expression "heterocyclyl" in the foregoing definitions is intended to include both aromatic and non-aromatic radicals. Examples of heteroaromatic radicals include pyridyl, pyrimidyl, triazinyl, thienyl, furyl, oxazolyl, isoxazolyl and thiazolyl and examples of non-aromatic radicals include partially and fully saturated variants of the above.

The expression "$C_1$–$C_6$ alkyl" refers to fully saturated straight or branched hydrocarbon chains having from one to six carbon atoms. Examples include methyl, ethyl, n-propyl, iso-propyl, t-butyl and n-hexyl. Expressions such as "alkoxy", "cycloalkyl", "alkylthio", "alkylsulphonyl", "alkylsulphinyl" and "haloalkyl" should be construed accordingly.

The expression "$C_2$–$C_6$ alkenyl" refers to a straight or branched hydrocarbon chain having from two to six carbon atoms and at least one carbon-carbon double bond. Examples include ethenyl, 2-propenyl and 2-hexenyl. Expressions such as cycloalkenyl, alkenyloxy and haloalkenyl should be construed accordingly.

The expression "$C_2$–$C_6$ alkynyl" refers to a straight or branched hydrocarbon chain having from two to six carbon atoms and at least one carbon-carbon triple bond. Examples include ethynyl, 2-propynyl and 2-hexynyl. Expressions such as cycloalkynyl, alkynyloxy and haloalkynyl should be construed accordingly.

Subclasses of the above include alkyl, alkenyl and alkynyl groups with up to 4 or up to 2 carbon atoms.

In the context of the present specification the terms "aryl" and "aromatic ring system" refer to ring systems which may be mono-, bi- or tricyclic. Examples of such rings include phenyl, naphthalenyl, anthracenyl and phenanthrenyl.

In the context of the present specification, the term "heteroaryl" refers to an aromatic ring system containing at least one heteroatom and consisting either of a single ring or of two or more fused rings. Preferably, single rings will contain up to 4 and bicyclic systems up to 5 heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, tetrazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3,4-oxatriazolyl, 1,2,3,5-oxatriazolyl, 1,2,3,4-thiatriazolyl, 1,2,3,5-thiatriazolyl, pyridyl, pyrimidinyl, pyridazinyl, pyrazinyl, 1,2,3-triazinyl, 1,2,4-triazinyl, 1,3,5-triazinyl, 1,2,4,5-tetrazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and inndolizinyl. Nitrogen atoms in the ring may be quaternised or oxidised.

In the context of the present specification, the term "fused saturated or partially saturated carbocyclic or heterocyclic ring system" refers to a fused ring system in which a 5- or 6-membered carbocyclic or heterocyclic ring which is not of aromatic character is fused to an aromatic or heteroaromatic ring system. Examples of such systems include benzoxazolinyl and benzodioxolyl.

Halogen atoms which $R^{13}$ and $R^{14}$ may represent and with which $R^1$, $R^7$ and A may be substituted include chlorine, bromine, fluorine and iodine.

The compounds described in WO 94/13652 and WO 95/33719 are chiral and so may exist in two enantiomeric forms. As is often the case with biologically active chiral compounds, one of the enantiomers is more active than the other. It would therefore be advantageous to be able to prepare the enantiomers separately.

Key intermediates in the synthesis of pyrrolidinone herbicides are hydroxy pyrrolidinones of formula II:

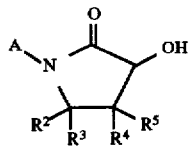

wherein $R^2$, $R^3$, $R^4$, $R^5$ and A are as defined in formula I.

The present inventors have found that if separate enantiomers of such compounds can be formed, it is possible to convert these enantiomers into enantiomeric forms of compounds of formula I.

Therefore, in a first aspect of the present invention there is provided a process for preparing a compound of formula IIa or IIb:

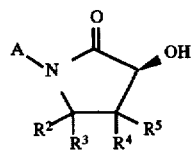

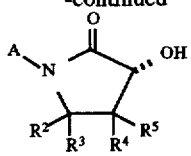

wherein $R^2$, $R^3$, $R^4$, $R^5$ and A are as defined in formula I; the process comprising the steps of:

(a) reacting a racemic mixture of a compound of formula II with a sterically hindered chiral esterifying agent to form enantiomers of formulae IIIa and IIIb:

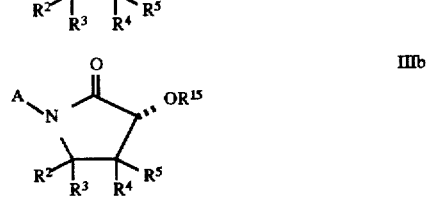

wherein $R^2$, $R^3$, $R^4$, $R^5$ and A are as defined in formula I and $R^{15}$ is a chiral sterically hindered residue;

(b) separating the diastereoisomers of formulae IIIa and IIIb; and (c) converting the diastereoisomers of formulae IIIa and IIIb separately to compounds of formulae IIa and IIb respectively by acid or base hydrolysis.

Typically, the chiral sterically hindered esterifying agent will be a compound such as a camphanic acid chloride which, when reacted with a compound of formula II, will give a separable 1:1 mixture of the two diastereomers IIIa and IIIb. When the esterifying agent is camphanic acid chloride, $R^{15}$ is camphanate.

Step (a) of the reaction may be conducted in an organic solvent, for example a halogenated solvent such as dichloromethane (DCM), at a temperature of from 0° to 50° C., typically at room temperature.

The separation process of step (b) may be achieved by any conventional means, for example fractional crystallisation or chromatography.

The hydrolysis of step (c) may also be achieved by conventional means but it has been found to be particularly convenient to use base mediated hydrolysis at a temperature of from 0° to 50° C., typically room temperature. Suitable bases for this reaction include alkali metal hydroxides such as sodium hydroxide. The reaction will usually be conducted in an organic solvent in order to ensure solubility of the ester of formula IIIa or IIIb. Typical solvents include ethers, especially cyclic ethers such as tetrahydrofuran (THF).

If required, the unwanted enantiomer of formula IIa or IIb may be inverted to give the preferred isomer. This may be achieved by, for example, reacting the compound of formula IIa or IIb with an esterifying agent, typically a carboxylic acid such as acetic or propionic acid in combination with a combination of agents such as triphenyl phosphine and diethyl azodicarboxylate (DEAD). The inversion reaction may be conducted in an organic solvent, typically an ether such as THF, and at a temperature of from 10° to 50° C., preferably room temperature. The resulting ester is then hydrolysed as described above.

Compounds of formula II as defined above may be prepared from compounds of formula IV:

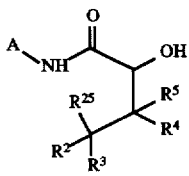

wherein $R^2$, $R^3$, $R^4$, $R^5$ and A are as defined in formula I and $R^{25}$ is a leaving group; under basic conditions.

The cyclisation must be carried out under basic conditions and these may be provided by a strong base such as an alkali metal hydride, alkoxide or hydroxide. Sodium hydride and sodium methoxide or ethoxide have been found to be particularly suitable for this purpose. The reaction may be carried out in any suitable solvent. The solvent chosen will, however, depend to a large extent upon the base which is used. Thus, when the base is an alkali metal hydride, the solvent may be an organic solvent such as THF, whilst for an alkoxide, the corresponding alcohol is more appropriate.

Although the group $R^{25}$ may be any leaving group, halogen atoms such as chloro, bromo and iodo are particularly suitable.

Compounds of formula IV may be prepared from compounds of formula V:

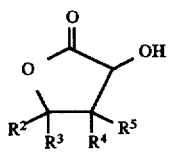

wherein $R^2$, $R^3$, $R^4$ and $R^5$ are as defined in formula I by reaction with a compound of formula VI:

A—NH$_2$      VI wherein A is as defined in formula I. This reaction is carried out in the presence of a reagent such as boron tribromide, aluminium trichloride, tin tetrachloride or titanium tetrachloride, the reaction may take place in an organic solvent such as dichloromethane or dichloroethane. Compounds of formulae V and VI are readily available or may be prepared by methods known in the art.

An alternative method for the preparation of compounds of formula II is by the reaction of a compound of formula V as defined above, wherein $R^2$ and $R^3$ are preferably hydrogen and $R^4$ and $R^5$ are hydrogen, with a compound of formula VI as defined above. The reaction may be conducted in the absence of a solvent and at a temperature of from about 100° to 300° C., preferably about 150° C. This reaction works particularly well for compounds in which A is phenyl or substituted phenyl.

In a second aspect of the invention, there is provided a process for preparing a compound of formula IIa or IIb as defined above; the process comprising heating a compound of formula Va or Vb:

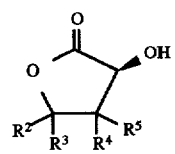

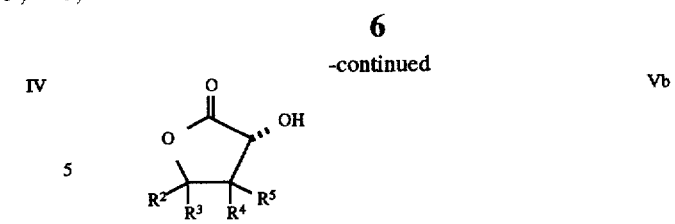

wherein $R^2$ and $R^3$ are as defined in formula I and $R^4$ and $R^5$ are hydrogen; with a compound of formula VI as defined above. The reaction may be conducted in the absence of a solvent and at a temperature of from about 100° to 300° C., preferably about 150° C. This reaction works particularly well for compounds in which A is phenyl or substituted phenyl. This aspect of the invention is particularly suitable for the production of compounds of formulae IIa and IIb in which $R^2$ and $R^3$ are hydrogen.

The compounds of formulae Va and Vb may be produced by the reduction and subsequent lactonistation of an appropriately protected L- or D-malic acid derivative, for example as described by Cammas et al, *Tetrahedron*, 1993, 4(8), 1925 and Gong et al, *J. Org. Chem.*, 1990, 55, 4763.

There are other methods for preparing compounds of formula II and therefore, in a third aspect of the invention, there is provided a process for preparing a compound of formula II so as to obtain an enantiomeric excess of a compound of formula IIa or IIb as defined above, the process comprising reacting a compound of formula VII:

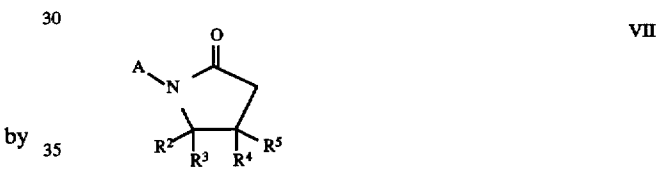

wherein $R^2$, $R^3$, $R^4$, $R^5$ and A are as defined in formula I; with a base followed by a sterically hindered chiral oxidising agent.

In the present invention, the term "enantiomeric excess" is defined as:

$$\frac{(\% \text{ major enantiomer}) - (\% \text{ minor enantiomer})}{(\% \text{ major enantiomer}) + (\% \text{ minor enantiomer})}$$

Using the process of this aspect of the invention, an enantiomeric excess (ee) of at least 10%, more usually at least 20% can be obtained.

The base is preferably a strong base such as lithium hexamethyldisilazide and the deprotonation reaction may take place in an organic solvent, for example an ether, particularly a cyclic ether such as THF. The reaction will often take place at a reduced temperature, for example from −100° to 10° C., usually at about −78° C.

Suitable sterically hindered chiral oxidising agents include compounds such as (+) camphoryl sulfonyl oxaziridine. This second step of the reaction may also be conducted at a reduced temperature, for example from −100° to 10° C., again usually at about −78° C. The solvent may be an organic solvent, for example a cyclic ether such as THF.

As briefly mentioned above, compounds of formula 11 are intermediates in the preparation of herbicides of formula I and, therefore, in a further aspect of the invention there is provided a process for the preparation of a compound of formula Ia or Ib:

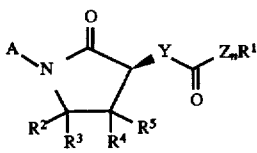

Ia

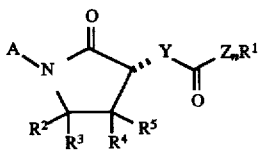

Ib wherein $R^1$, $R^2$, $R^3$, $R^4$, $R^5$, Y, Z, n and A are as defined in formula I;

the process comprising preparing a compound of IIa or IIb by a process according to the first, second or third aspect of the invention and converting the compound of formula IIa or IIb to a compound of formula Ia or Ib by any suitable method.

Examples of methods for converting compounds of formula II to compounds of formula I are described in WO 94/13652 and UK Patent Application No 9501158 but any method may be used.

For example, a compound of formula II may be converted to a compound of formula I by reaction with a compound of formula IX, X, XI or XII:

IX

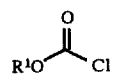

X $R^1-N=C=O$

XI

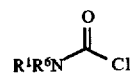

XII wherein $R^1$ and $R^6$ are as defined for formula I; resulting in the production of compounds of formula I in which Y is O and in which n is 0, Z is O, Z is NH and Z is $NR^6$ respectively.

Similarly, a compound of formula II may be reacted with a compound of formula XIII:

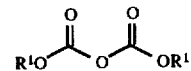

XIII wherein $R^1$ is as defined for formula I. This gives compounds of formula I in which Y and Z are both O. These reactions may be conducted in an organic solvent such as dichloromethane.

Compounds of formula II may be converted into compounds of formula XIV:

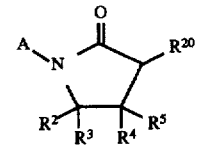

XIV wherein $R^2$, $R^3$, $R^4$, $R^5$ and A are as defined for formula I and $R^{20}$ is chloro, methane sulfonyloxy or toluene sulfonyloxy. The compounds in which $R^{20}$ is methane sulfonyloxy or toluene sulfonyloxy may be obtained by reaction with methane sulfonyl chloride or toluene sulfonyl chloride as appropriate although, in some cases, the compound in which $R^{20}$ is chloro may be obtained, particularly in the reaction with methane sulfonyl chloride. The reaction may be conducted at a temperature of from 0° to 30° C., usually at about 5° C., in an organic solvent such as dichloromethane and in the presence of a base such as triethylamine.

Compounds of formula XIV may be converted into compounds of formula XV:

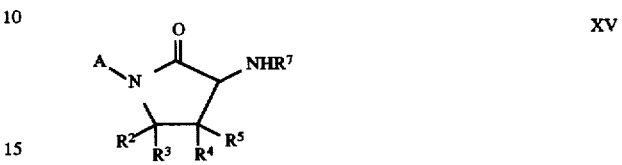

XV wherein $R^2$, $R^3$, $R^4$, $R^5$, $R^7$ and A are as defined for formula I; by reaction with an alkali metal azide such as sodium azide to give the equivalent azide compound followed by reduction of the azide by any known method, for example using a 1,3-propane dithiol in a basic solvent, to give the appropriate compound of formula XV. The first step may be carried out at a temperature of from 0° to 30° C., but preferably at room temperature, in a solvent such as dimethyl formamide (DMF). The conversion of the azide to a compound of formula XV is preferably carried out under an inert atmosphere such as nitrogen at 0° to 30° C., most suitably at room temperature. The solvent may be an amine such as triethylamine.

Alternatively, a compound of formula XIV may be reacted with ammonia or an amine of formula $NH_2R^7$. The reaction may be carried out at a temperature of from 0° to 80° C., preferably from 0° to 50° C. It is often the case that the reaction is initiated at 0° C. and subsequently allowed to warm to room temperature after most of the reactant has been converted to product. Usually, the reaction will take place in an organic solvent, particularly an ether such as diethyl ether or THF.

Compounds of formula XV may be converted to compounds of formula I in which Y is $NR^7$ by reaction with a compound of formula IX, X, XI or XII using the reaction conditions described above for the conversion of compounds of formula II to compounds of formula I.

Compounds of formula XIV in which $R^{20}$ is halogen may be converted to compounds of formulae XVI:

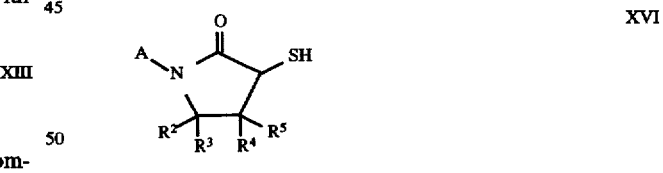

XVI by reaction firstly with a thioacid of formula XVII:

XVII wherein $R^1$ is as defined for formula I; to give a compound of formula I in which Y is S and n is 0; followed by reaction with ammonia in a protic solvent such as methanol. The second step may be carried out at a temperature of −10° to 10° C., usually about 0° C. The compound of formula XVI may be converted to a compound of formula I by reaction with a compound of formula IX, X, X/or XII as described above for compounds of formula II and compounds of formula XV.

Compounds of formula I may also be converted to other compounds of formula I. For example, bridged compounds of formula I in which Y is NR$^7$, Z is NR$^6$ and R$^6$ and R$^7$ form a bridge may be synthesised in a variety of ways.

Compounds in which the bridge is represented by the formula —Q$^1$—C(=O)— may be synthesised from compounds of formula I in which Z is NH and Y is N—Q$^1$—C(=O)—L in which L is a leaving group such as methoxy, ethoxy or chloro, and Q$^1$ is as defined above. The reaction is preferably carried out in the presence of a strong base such as sodium hydride, suitably in a solvent such as THF. Usually, the reaction temperature will be in the range of 0° to 80° C., preferably room temperature. They may alternatively be synthesised from compounds of formula XIV in which R$^{20}$ is a leaving group such as I or Br by reaction with an imidazolinedione of formula XVIII:

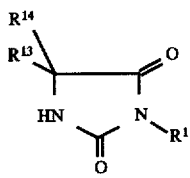
XVIII wherein R$^{13}$ and R$^{14}$ independently represent hydrogen or C$_1$-C$_4$ alkyl. The reaction is carried out in an organic solvent such as DMF or THF, in the presence of a strong base such as sodium hydride.

Compounds in which the bridge is represented by the formula —C(=O)—C(=O)— or —C(=O)—Q$^2$—C(=O)— may be synthesised from compounds of formula I in which both Y and Z are NH by reaction with a compound of formula LC(=O)—C(=O)L or LC(=O)—Q$^2$—C(=O)L in which Q$^2$ and L are as defined above. The reaction may be carried out in an organic solvent such as toluene at a temperature of from 30° to 120° C. Often, the reaction will be conducted at a temperature of about 80° C.

Compounds in which the bridge is represented by the formula —HC=CH— may be synthesised from compounds of formula I in which Z is NH and Y is NCH$_2$CHL$_2$, wherein L is a leaving group as defined above. The reaction may be carried out in a solvent such as THF under acidic conditions which may be provided by the presence of an aqueous inorganic acid such as hydrochloric acid. The reaction temperature may be from 5° to 50° C. but will, in most cases, be room temperature.

Compounds of formula I in which the bridge is represented by the formula —CH=CH— may be converted to compounds of formula I in which the bridge is represented by —CH$_2$—CH$_2$— by reduction, for example hydrogenation over a palladium or platinum catalyst. Catalytic hydrogenations may be carried out in a solvent such as ethyl acetate. The reaction usually proceeds at an acceptable rate at room temperature and at a pressure of from 1 to 5 bar.

Compounds in which the bridge is represented by the formula —C(=O)—CH$_2$— may be synthesised from compounds of formula I in which Y and Z are both NH by reaction with CHO—CHO. The reaction may be conducted under acidic conditions which may be provided by the presence of a catalytic amount of, for example, p-toluene sulphonic acid. An example of a suitable reaction solvent is toluene and the reaction is preferably carried out under Dean and Stark conditions at a temperature of from about 80° to 120° C., typically at 110° C. Similar reaction conditions may also be used for the synthesis of compounds of formula I in which the bridge is represented by the formula —CH$_2$—O—CH$_2$—. However, in this case, paraformaldehyde is used in place of CHO—CHO. This particular reaction may be adapted by those skilled in the art for the synthesis of other bridged compounds.

All of the reactions described above for the conversion of compounds of formula II to compounds of formula I can, of course, be applied to enantiomers of formulae IIa and IIb so as to produce enantiomers of formulae Ia and Ib.

The compounds of formulae Ia and Ib are useful as herbicides and show activity against a broad range of weed species including monocotyledonous and dicotyledonous species. They show some selectivity towards certain species, and may be used, for example, as selective herbicides in soya, maize and rice crops. The compounds of formulae Ia and Ib may be used on their own to kill or severely damage plants, but are preferably used in the form of a composition comprising a compound of formula Ia or Ib in admixture with a carrier comprising a solid or liquid diluent.

The invention will now be described in greater detail with reference to the following examples.

EXAMPLE 1

Asymmetric oxidation of N-(3-trifluoromethyl)phenyl-2-pyrrolidinone to 3-hydroxy-N-(3-trifluoromethyl) phenyl-2-pyrrolidinone To a solution of N-(3-trifluoromethyl)phenyl-2-pyrrolidinone (0.50 g) in THF (20 ml) at -78° C. was added lithium hexamethyldisilazide (5.0 ml of a 1M solution in hexane). The colour changed from yellow to red. (+)-Camphoryl sulfonyl oxaziridine (1.14 g) in THF (5.0 ml) was added and the colour changed back to yellow. The mixture was stirred for 30 min at -78° C. and then added to sat. NH$_4$Cl (aq). Ether was added, the organic layer separated, dried (MgSO$_4$) and evaporated. Cold ether was added to the residual oil and the solid imine by-product separated. The residue was purified by column chromatography eluting with ethyl acetate/hexane to give 3-hydroxy-N-(3-trifluoromethyl)phenyl-2-pyrrolidinone (0.274 g).

$^{19}$F NMR of racemic 3-hydroxy-N-(3-trifluoromethyl) phenyl-2-pyrrolidinone ( 10 mg) in CDCl$_3$ (1 ml) containing (R)-(-)-(9-anthryl)-2,2,2-trifluoroethanol (0.10 g) as a chiral solvent gave two distinct singlets in a 1:1 ratio corresponding to the two enantiomeric alcohols. Analysis of the oxidation product in a similar manner showed two singlets (-72.31 and -72.33 with CFCl$_3$ as internal reference), but in an intensity ratio of 5:3, indicating an enantiomeric excess (ee) of approximately 20%. At this stage it was not possible to determine which enantiomer had been formed preferentially, although it later became apparent that the downfield signal (-72.31) corresponds to the (R) enantiomer.

An alternative route to both enantiomers is described in Example 2.

EXAMPLE 2

Preparation of (3R)3-$^t$butylcarbonyloxy-N-(3-trifluoromethyl)phenyl-2-pyrrolidinone and (3S) 3-$^t$butylcarbonyloxy-N-(3-trifluoromethyl)phenyl-2-pyrrolidinone a) (3R) 3-Hydroxy-N-(3-trifluoromethyl)phenyl-2-pyrrolidinone camphanic ester and (3S) 3-hydroxy-N-(3-trifluoromethyl)phenyl-2-pyrrolidinone camphanic ester A mixture of racemic 3-hydroxy-N-(3-trifluoromethyl) phenyl-2-pyrrolidinone (0.15 g), triethylamine (0.083 ml) and (1S)-(-)-camphanic acid chloride (0.134 g) in dichloromethane (10 ml) was stirred at room temperature overnight. The mixture was then washed with 2N HCl (aq), sat. NaHCO$_3$ (aq) and dried (MgSO$_4$) to give a yellow oil after evaporation of the solvent. The oil was purified by column chromatography, eluting with ether/hexane (1:1) followed by ether/hexane (2:1) to give, in order of elution, (3R) 3-hydroxy-N-(3-trifluoromethyl)phenyl-2-pyrrolidinone camphanic ester as a gum (79 mg), $^1$H NMR (CDCl$_3$) 5.75 (1H, t, H-3) inter alia, followed by (3S) 3-hydroxy-N-(3-trifluoromethyl)phenyl-2-pyrrolidinone camphanic ester as a colourless solid (43 mg), $^1$H NMR (CDCl$_3$) 5.73 (1H, t, H-3) inter alia.

On a larger scale (50.225 g) the pure (3S) isomer (21.12 g) could be isolated by fractional crystallisation of the mixture of camphanic acid esters from ether/DCM/hexane. The remaining mixture (which contained mainly (3R)) was taken through a similar inversion process, via the acetate, to that outlined in Example 3. This mixture of camphanic acid esters was saponified, the alcohols inverted by Mitsonobu reaction giving a mixture of predominantly the (3S) acetate, $^1$H NMR (CDCl$_3$) 2.08–2.22 (4H, m), 2.66–2.80 (1H, m), 3.82–3.96 (2H, m), 5.48 (1H,t), 7.43 (1H,d), 7.54 (1H, t), 7.93 (1H, s), 7.94 (1H, d) inter alia. Subsequent hydrolysis, re-esterification with (1S)-(–)-camphanic chloride and crystallisation of the major isomer, gave further pure (3S) 3-hydroxy-N-(3-trifluoromethyl)phenyl-2-pyrrolidinone camphanic ester.

b) (3R) 3-Hydroxy-N-(3-trifluoromethyl)phenyl-2-pyrrolidinone and (3S) 3-hydroxy-N-(3-trifluoromethyl)phenyl-2-pyrrolidinone To a solution of (3R) 3-hydroxy-N-(3-trifluoromethyl)phenyl-2-pyrrolidinone camphanic ester (63 mg) in THF (5 ml) was added NaOH (12 mg) in water (1.2 ml). An immediate colour change was observed. Tlc analysis indicated that the reaction was complete. The mixture was acidified with 2N HCl (aq) and extracted with ethyl acetate. The organic phase was washed with sat. NaHCO$_3$ (aq), dried (MgSO$_4$) and evaporated to give (3R) 3-hydroxy-N-(3-trifluoromethyl)phenyl-2-pyrrolidinone (40 mg). Analysis of the product by $^{19}$F NMR (as described in Example 1) gave only one peak indicating an enantiomerically pure product.

In an analogous reaction, the (3S) isomer (43 mg) was saponified to the corresponding (3S) alcohol (26 mg).

c) (3R) 3-$^t$Butylcarbonyloxy-N-(3-trifluoromethyl)phenyl-2-pyrrolidinone and (3S) 3-$^t$butylcarbonyloxy-N-(3-trifluoromethyl)phenyl-2-pyrrolidinone A mixture of (3R) 3-hydroxy-N-(3-trifluoromethyl)phenyl-2-pyrrolidinone (30 mg), triethylamine (0.017 ml) and $^t$butyl isocyanate (0.027 ml) in dichloromethane (5 ml) was stirred at room temperature. After 4 hours further $^t$butyl isocyanate (0.027 ml) was added and stirring continued for 72 hours. After evaporation of the solvent, chromatography on silica, eluting with ethyl acetate/hexane (1:3) gave the (3R) carbamate (17 mg) $[a]_D$=–18° (c=0.327 g/100 ml, DCM.

In an analogous reaction, the (3S) alcohol (26 mg) gave the (3S) carbamate (24 mg) $[a]_D$=–17° (c=0.426 g/100 ml DCM).

The (3S) carbamate prepared via the larger scale crystallisation route gave $[a]_D$=–18° (c=0.460 g/100 ml, DCM). Analysis by chiral phase HPLC on a No. 565 L-phenylglycine column, eluting with hexane/THF/MeCN (90:10:1) indicated an ee of 90%.

EXAMPLE 3

Preparation of (3R) 3-$^t$butylcarbonyloxy-N-(3-trifluoromethoxy)phenyl-2-pyrrolidinone and (3S) 3-$^t$butylcarbonyloxy-N-(3-trifluoromethoxy)phenyl-2-pyrrolidinone a) (3R) 3-Hydroxy-N-(3-trifluoromethoxy)phenyl-2-pyrrolidinone camphanic ester and (3S) 3-hydroxy-N-(3-trifluoromethoxy)phenyl-2-pyrrolidinone camphanic ester A mixture of racemic 3-hydroxy-N-(3-trifluoromethoxy)phenyl-2-pyrrolidinone (0.511 g), triethylamine (0.28 ml) and (1S)-(–)-camphanic acid chloride (0.424 g) in dichloromethane (25 ml) was stirred for 18 hours at room temperature. Further camphanic acid chloride (0.424 g) was added and the mixture stirred for a further 24 hours. The reaction was washed with 2N HCl (aq), sat. NaHCO$_3$ (aq) and dried (MgSO$_4$). Evaporation and chromatography on silica, eluting with ethyl acetate/hexane (1:4) gave, in order of elution, (3R) 3-hydroxy-N-(3-trifluoromethoxy)phenyl-2-pyrrolidinone camphanic ester (0.125 g), $^1$H NMR (CDCl$_3$) 5.75 (1H, t, H-3) inter alia, followed by (3S) 3-hydroxy-N-(3-trifluoromethoxy)phenyl-2-pyrrolidinone camphanic ester as a colourless solid, $^1$H NMR (CDCl$_3$) 5.73 (1H, t, H-3) inter alia. The latter compound was submitted to single crystal x-ray analysis which confirmed the structure unambiguously. This determination was used to infer the configuration of compounds made directly from this camphanic acid ester, its enantiomer and by analogy, the N-(3-trifluoromethyl)phenyl series.

On a larger scale (50 g of the 3-hydroxy pyrrolidinone), the pure (3S) camphanic acid ester (25.9 g) could be isolated by fractional crystallisation of the mixture of camphanic acid esters from ether/DCM/hexane. The pure (3R) camphanic acid ester (7 g) could be isolated by further crystallisation of the residue using ether.

b) (3R) 3-Hydroxy-N-(3-trifluoromethoxy)phenyl-2-pyrrolidinone and (3S) 3-hydroxy-N-(3-trifluoromethoxy)phenyl-2-pyrrolidinone Saponification of the camphanic acid esters was achieved in an analogous manner to that described in Example 2b). Thus the (3R) camphanic acid ester (0.125 g) was hydrolysed to the (3R) hydroxy derivative (66 mg). $^{19}$F NMR analysis of the product (as described in Example 1) showed two peaks in a ratio of 100:3 (–59.22 and –59.23 with CFCl$_3$ as internal standard) indicating an ee of 94%. The (3S) camphanic acid ester (0.282 g) was similarly hydrolysed to the (3S) hydroxy derivative (0.136 g) $[a]_D$=–46° (c=0.220 g/100 ml, DCM). $^{19}$F NMR analysis of the product (as described in Example 1) showed two peaks in a ratio of 5:100 (–59.22 and –59.24 with CFCl$_3$ as internal standard) indicating an ee of 90%.

The (3S) hydroxy product from the larger scale crystallization route (see step a)) gave two peaks in the ratio of 4:96 by $^{19}$F NMR analysis, indicating an ee of 92%. The (3R) alcohol could be inverted to the (3S) isomer by the method outlined in step d) below.

c) (3R) 3-$^t$Butylcarbonyloxy-N-(3-trifluoromethoxy)phenyl-2-pyrrolidinone and (3S) 3-$^t$butylcarbonyloxy-N-(3-trifluoromethoxy)phenyl-2-pyrrolidinone The (3R) alcohol (66 mg), prepared as described in step b) was converted to the corresponding carbamate (24 mg) $[a]_D$=+7° (c=0.400 g/100 ml, DCM) by an analogous procedure to that described in Example 2c). Similarly, the (3S) alcohol (136 mg) gave the corresponding carbamate (68 mg) $[a]_D$=–11° (c=0.400 g/100 ml, DCM).

The (3S) carbamate prepared from the product of the larger scale crystallisation route gave $[a]_D$=–18° (c=0.400 g/100 ml, DCM). Analysis by chiral phase HPLC on a No. 565 L-phenylglycine column, eluting with hexane/THF/MeCN (90:10:1) indicated an ee of 94%.

d) Conversion of (3R) 3-hydroxy-N-(3-trifluoromethoxy)phenyl-2-pyrrolidinone to (3S) 3-hydroxy-N-(3-trifluoromethoxy)phenyl-2-pyrrolidinone i. (3S) 3-Acetoxy-N-(3-trifluoromethoxy)phenyl-2-pyrrolidinone.

To a solution of (3R) 3-hydroxy-N-(3-trifluoromethoxy)phenyl-2-pyrrolidinone (0.93 g) in THF (20 ml) was added triphenylphosphine (1.00 g) and acetic acid (0.24 g). Diethyl azodicarboxylate (DEAD) (0.69 g) in THF (10 ml) was added dropwise over 30 min. After a further 72 hours at room temperature, the mixture was evaporated and purified by column chromatography, eluting with ethyl acetate/hexane (1:2) to give the partially purified (3S) acetate (0.80 g), $^1$H NMR (CDCl$_3$) 2.10–2.22 (4H, m), 2.67–2.79 (1H, m), 3.78–3.92 (2H, m), 5.49 (1H,t), 7.05 (1H, dd), 7.40 (1H, t), 7.57 (1H, dd), 7.68 (1H, s).

ii. (3S) 3-Hydroxy-N-(3-trifluoromethoxy)phenyl-2-pyrrolidinone.

The acetate (0.80 g) prepared as in step i. was dissolved in THF (10 ml) and NaOH (0.20 g) in water (10 ml) added. After 20 min the mixture was extracted with ethyl acetate. The organic phase was washed with water, dried (MgSO$_4$) and evaporated. The residue was recrystallised from ethyl acetate/hexane to give the pure (3S) hydroxy derivative (0.503 g). $^{19}$F NMR analysis of the product (as described in Example 1) showed two peaks in a ratio of 4:96, indicating an ee of 92% (similar to that obtained in Example 3b)), confirming the (3S) assignment.

EXAMPLE 4

Preparation of (3S) 3-($^t$butylcarbamoyl-N-methylamino)-N-(3-trifluoromethoxy)phenyl-2-pyrrolidinone and (3R) 3-($^t$butylcarbamoyl-N-methylamino)-N-(3-trifluoromethoxy)phenyl-2-pyrrolidinone a) (3R) 3-Methanesulfonyloxy-N-(3-trifluoromethoxy)phenyl-2-pyrrolidinone (3R) 3-Hydroxy-N-(3-trifluoromethoxy)phenyl-2-pyrrolidinone (0.45 g) was dissolved in DCM (10 ml) and cooled to 0° C. To this was added triethylamine (0.25 ml) followed by methanesulfonyl chloride (0.14 ml). The mixture was stirred at 0° C. for 30 min and then allowed to warm to room temperature and stirred for a further 90 min. The mixture was diluted with DCM, washed with water (×2), brine and dried (MgSO$_4$). Evaporation of the solvent gave the mesylate (0.59 g) as clear oil which crystallised.

In an analogous reaction, (3S) 3-hydroxy-N-(3-trifluoromethoxy)phenyl-2-pyrrolidinone (0.594 g) gave the corresponding (3S) mesylate (0.770 g).

b) (3S) 3-(N-Methylamino)-N-(3-trifluoromethoxy)phenyl-2-pyrrolidinone and (3R) 3-(N-methylamino)-N-(3-trifluoromethoxy)phenyl-2-pyrrolidinone (3R) 3-Methanesulfonyloxy-N-(3-trifluoromethoxy)phenyl-2-pyrrolidinone (0.59 g), prepared as described in step a), was dissolved in THF (15 ml) and cooled to 0° C. Methylamine gas was bubbled through the solution for 15 min. The mixture was allowed to warm to room temperature for 20 min. The solution was treated with methylamine for a further 20 min and left to stand for 18 hours. Further methylamine was bubbled, through for 20 min and the reaction left for 6 hours. The volatiles were removed under reduced pressure. The residue was taken up in ethyl acetate, washed with water (×3), brine, dried (MgSO$_4$) and the solvent evaporated. The residue was purified by chromatography, eluting with ethyl acetate/hexane (2:3 rising to 1:1 ), to give the (3S) amine (0.321 g) as an off white solid. Analysis of the product by $^{19}$F NMR (as described in Example 1) showed an ee of 86%.

In an analogous reaction, (3S) 3-methanesulfonyloxy-N-(3-trifluoromethoxy)phenyl-2-pyrrolidinone (0.77 g) gave the (3R) amine (0.52 g). Analysis of the product by $^{19}$F NMR (as described in Example 1) showed an ee of 74%.

c) (3S) 3-($^t$Butylcarbamoyl-N-methylamino)-N-(3-trifluoromethoxy)phenyl-2-pyrrolidinone and (3R) 3-($^t$butylcarbamoyl-N-methylamino)-N-(3-trifluoromethoxy)phenyl-2-pyrrolidinone (3S) 3-(N-Methylamino)-N-(3-trifluoromethoxy)phenyl-2-pyrrolidinone (0.36 g) prepared as in step b) was dissolved in DCM (5 ml) and treated with triethylamine (0.18 ml) followed by $^t$butyl isocyanate. The reaction was stirred at room temperature for 18 hours, diluted with DCM, washed with 2N HCl (aq), brine and dried (MgSO$_4$). The solvent was evaporated and the residue purified by chromatography on silica, eluting with EtOAc/hexane (7:3) to give the (3S) urea (0.35 g) as a colourless solid, mp 127°–130° C. Analysis of the product by $^{19}$F NMR (as described in Example 1) showed an ee of 76%.

In an analogous reaction, (3R) 3-(N-methylamino)-N-(3-trifluoromethoxy)phenyl-2-pyrrolidinone (0.293 g) gave the corresponding (3R) urea (0.30 g) as a colourless solid after recrystallisation from ethyl acetate, mp 135°–137° C. Analysis of the product by $^{19}$F NMR (as described in Example 1) showed an ee of 44%. The recrystallisation enriches the product in the minor enantiomer.

EXAMPLE 5

Preparation of (3S) 3-($^t$butylacetyl-N-methylamino)-N-(3-trifluoromethoxy)phenyl-2-pyrrolidinone and (3R) 3-($^t$butylacetyl N-methylamino)-N-(3-trifluoromethoxy)phenyl-2-pyrrolidinone (3S) 3-(N-Methylamino)-N-(3-trifluoromethoxy)phenyl-2-pyrrolidinone (0.31 g) (prepared as in Example 4b)) was dissolved in DCM (10 ml). To this was added triethylamine (0.17 ml), followed by $^t$butylacetyl chloride (0.17 ml). The reaction was stirred at room temperature for 20 min, diluted with DCM, washed with water (×3), brine and dried (MgSO$_4$). Evaporation of the solvent and purification of the residue by chromatography on silica gave the (3S) amide (0.395 g) as a colourless solid, mp 88°–90° C. Analysis of the product by $^{19}$F NMR (as described in Example 1) showed an ee of 86%.

In an analogous reaction, (3R) 3-(N-methylamino)-N-(3-trifluoromethoxy)phenyl-2-pyrrolidinone (0.200 g) gave the corresponding (3R) amide (0.254 g) as a colourless solid, mp 86°–88° C. Analysis of the product by $^{19}$F NMR (as described in Example 1) showed an ee of 74%.

EXAMPLE 6

Alternative Preparation of (3R) 3-hydroxy-N-(3-trifluoromethoxy)phenyl-2-pyrrolidinone a) (3R) 3-Hydroxytetrahydrofuran-2-one Crude (2R) Methyl 2,4-dihydroxybutanoate (3.57 g, *) was dissolved in HCl (2M, 18 ml) and heated at reflux for 3 hours, until GC indicated a single product. The crude product was purified by Kugelruhr distillation, to give the furanone as an oil (1.34 g) b.p. 150° C. (2.4×10$^{-2}$ mbar).

$^1$H NMR (CDCl$_3$) 2.15 (1H, m), 2.62 (1H, m), 3.82 (2H, m), 4.15 (1H, br), 4.55 (2H, dd), 7.45 (2H, m), 7.88 (2H, m).

* Produced from L-malic acid according to the methods of Cammas et al, *Tetrahedron*, 1993, 4(8), 1925 and Gong et al, *J. Org. Chem.*, 1990, 55, 4763.

b) (3R) 3-Hydroxy-N-(3-trifluoromethoxy)phenyl-2-pyrrolidinone (3R) 3-Hydroxytetrahydrofuran-2-one (500 mg) and 3-trifluoromethylaniline (950 mg) were mixed and stirred at 150° C. for a total of 35 hours until GC and $^1$H NMR showed that the reaction had proceeded to completion. Purification of the crude product on silica, eluting with EtOAc/hexane (8:2) gave the (3R) hydroxy derivative (790 mg). Analysis of the product by HPLC showed an enantiomer ratio of 92:8, indicating an ee of 84%.

We claim:

1. A process for the preparation of a compound of formula IIa or IIb:

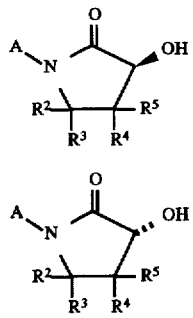

wherein
$R^2$, $R^3$, $R^4$ and $R^5$ independently represent hydrogen or $C_1$–$C_4$ alkyl;

A is an aromatic or heteroaromatic ring system optionally substituted with one or more substituents selected from halogen, $C_1$–$C_{10}$ hydrocarbyl, $S(O)_p(C_1$–$C_{10}$ hydrocarbyl), cyano, nitro, SCN, $SiR^c_3$ where each $R^c$ is independently $C_1$–$C_4$ alkyl or phenyl, $COR^8$, $CR^8NOR^9$, NHOH, $ONR^8R^9$, $SF_5$, $COOR^8$, $SO_2NR^8R^9$, $OR^{10}$ and $NR^{11}R^{12}$; and in which any ring nitrogen atom may be quaternised or oxidised;

alternatively, any two substituents of the group A may combine to form a fused 5- or 6- membered saturated or partially saturated carbocyclic or heterocyclic ring in which any carbon or quaternised nitrogen atom may be substituted with any of the groups mentioned above for A or in which a ring carbon atom may be oxidised;

p is 0, 1 or 2;

$R^8$ and $R^9$ independently represent hydrogen or $C_1$–$C_{10}$ hydrocarbyl;

$R^{10}$ is hydrogen, $C_1$–$C_{10}$ hydrocarbyl, $SO_2(C_1$–$C_{10}$ hydrocarbyl), CHO, $CO(C_1$–$C_{10}$ hydrocarbyl), COO $(C_1$–$C_{10}$ hydrocarbyl) or $CONR^8R^9$;

$R^{11}$ and $R^{12}$ independently represent hydrogen, $C_1$–$C_{10}$ hydrocarbyl, $O(C_1$–$C_{10}$ hydrocarbyl), $SO_2(C_1$–$C_{10}$ hydrocarbyl), CHO, $CO(C_1$–$C_{10}$ hydrocarbyl), COO $(C_1$–$C_{10}$ hydrocarbyl) or $CONR^8R^9$;

any of the hydrocarbyl groups within the group A may optionally be substituted with halogen, hydroxy, $SO_2NR^aR^b$ where $R^a$ and $R^b$ independently represent hydrogen or $C_1$–$C_6$ alkyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or $C_1$–$C_{10}$ hydrocarbyl optionally substituted with halogen, alkoxycarbonyl wherein the alkoxy group may have from 1 to 6 or more carbon atoms or aryl;

the process comprising the steps of:

a. reacting a racemic mixture of a compound of formula II:

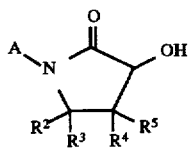

wherein $R^2$, $R^3$, $R^4$, $R^5$ and A are as defined for formulae IIa and IIb;

with a sterically hindered chiral esterifying agent at a temperature of from 0° to 50° C. to form enantiomers of formulae IIIa and IIIb:

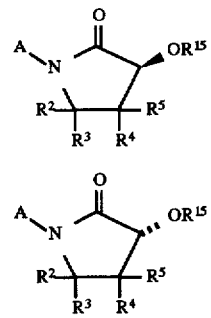

wherein $R^2$, $R^3$, $R^4$, $R^5$ and A are as defined for formulae IIa and IIb and $R^{15}$ is a chiral sterically hindered residue;

b. separating the diastereomers of formulae IIIa and IIIb by any suitable means; and c. converting the diastereomers of formulae IIIa and IIIb separately to compounds of formulae IIa and IIb respectively by acid or base hydrolysis.

2. A process as claimed in claim 1, wherein the chiral, sterically hindered esterifying agent is a camphanic acid chloride and $R^{15}$ is camphanate.

3. A process as claimed in claim 1, wherein the hydrolysis of step (c) is base mediated hydrolysis.

4. A process for the preparation of a compound of formula IIa or IIb:

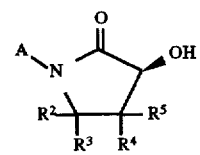

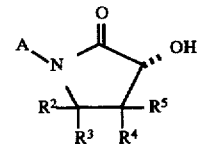

wherein
$R^2$, $R^3$, $R^4$ and $R^5$ independently represent hydrogen or $C_1$–$C_4$ alkyl;

A is an aromatic or heteroaromatic ring system optionally substituted with one or more substituents selected from halogen, $C_1$–$C_{10}$ hydrocarbyl, $S(O)_p(C_1$–$C_{10}$ hydrocarbyl), cyano, nitro, SCN, $SiR^c_3$ where each $R^c$ is independently $C_1$–$C_4$ alkyl or phenyl, $COR^8$, $CR^8NOR^9$, NHOH, $ONR^8R^9$, $SF_5$, $COOR^8$, $SO_2NR^8R^9$, $OR^{10}$ and $NR^{11}R^{12}$; and in which any ring nitrogen atom may be quaternised or oxidised;

alternatively, any two substituents of the group A may combine to form a fused 5- or 6- membered saturated or partially saturated carbocyclic or heterocyclic ring in which any carbon or quaternised nitrogen atom may be substituted with any of the groups mentioned above for A or in which a ring carbon atom may be oxidised;

p is 0, 1 or 2;

$R^8$ and $R^9$ independently represent hydrogen or $C_1$–$C_{10}$ hydrocarbyl;

$R^{10}$ is hydrogen, $C_1$–$C_{10}$ hydrocarbyl, $SO_2(C_1$–$C_{10}$ hydrocarbyl) CHO, $CO(C_1$–$C_{10}$ hydrocarbyl), COO $(C_1$–$C_{10}$ hydrocarbyl) or $CONR^8R^9$;

$R^{11}$ and $R^{12}$ independently represent hydrogen, $C_1$–$C_{10}$ hydrocarbyl, $O(C_1$–$C_{10}$ hydrocarbyl), $SO_2(C_1$–$C_{10}$ hydrocarbyl), CHO, $CO(C_1$–$C_{10}$ hydrocarbyl), COO $(C_1$–$C_{10}$ hydrocarbyl) or $CONR^8R^9$;

any of the hydrocarbyl groups within the group A may optionally be substituted with halogen, hydroxy, $SO_2NR^aR^b$ where $R^a$ and $R^b$ independently represent hydrogen or $C_1$–$C_6$ alkyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or $C_1$–$C_{10}$ hydrocarbyl optionally substituted with halogen, alkoxycarbonyl wherein the alkoxy group may have from 1 to 6 or more carbon atoms or aryl; the process comprising heating a compound of formula Va or Vb:

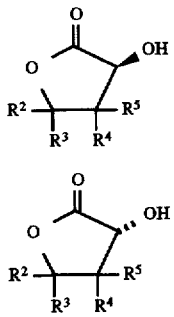

Va

Vb wherein $R^2$ and $R^3$ are as defined for formulae IIa and IIb and $R^4$ and $R^5$ are hydrogen; with a compound of formula VI:

A—NH$_2$  VI wherein A is as defined for formulae IIa and IIb at a temperature of from about 100° to 300° C.

5. A process as claimed in claim 1 or claim 4 further including the step of inverting the unwanted enantiomer of formula IIa or IIb to give the preferred isomer.

6. A process for preparing a compound of formula II so as to obtain an enantiomeric excess of a compound of formula IIa or IIb:

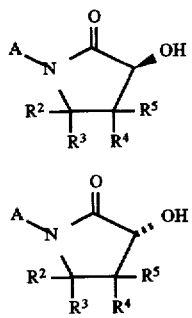

IIa

IIb wherein $R^2$, $R^3$, $R^4$ and $R^5$ independently represent hydrogen or $C_1$–$C_4$ alkyl;

A is an aromatic or heteroaromatic ring system optionally substituted with one or more substituents selected from halogen, $C_1$–$C_{10}$ hydrocarbyl, $S(O)_p(C_1$–$C_{10}$ hydrocarbyl), cyano, nitro, SCN, $SiR^c_3$ where each $R^c$ is independently $C_1$–$C_4$ alkyl or phenyl, $COR^8$, $CR^8NOR^9$, NHOH, $ONR^8R^9$, $SF_5$, $COOR^8$, $SO_2NR^8R^9$, $OR^{10}$ and $NR^{11}R^{12}$; and in which any ring nitrogen atom may be quaternised or oxidised;

alternatively, any two substituents of the group A may combine to form a fused 5- or 6- membered saturated or partially saturated carbocyclic or heterocyclic ring in which any carbon or quaternised nitrogen atom may be substituted with any of the groups mentioned above for A or in which a ring carbon atom may be oxidised;

p is 0, 1 or 2;

$R^8$ and $R^9$ independently represent hydrogen or $C_1$–$C_{10}$ hydrocarbyl;

$R^{10}$ is hydrogen, $C_1$–$C_{10}$ hydrocarbyl, $SO_2(C_1$–$C_{10}$ hydrocarbyl) CHO, $CO(C_1$–$C_{10}$ hydrocarbyl), COO $(C_1$–$C_{10}$ hydrocarbyl) or $CONR^8R^9$;

$R^{11}$ and $R^{12}$ independently represent hydrogen, $C_1$–$C_{10}$ hydrocarbyl, $O(C_1$–$C_{10}$ hydrocarbyl), $SO_1(C_1$–$C_{10}$ hydrocarbyl), CHO, $CO(C_1$–$C_{10}$ hydrocarbyl), COO $(C_1$–$C_{10}$ hydrocarbyl) or $CONR^8R^9$;

any of the hydrocarbyl groups within the group A may optionally be substituted with halogen, hydroxy, $SO_2NR^aR^b$ where $R^a$ and $R^b$ independently represent hydrogen or $C_1$–$C_6$ alkyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or $C_1$–$C_{10}$ hydrocarbyl optionally substituted with halogen, alkoxycarbonyl wherein the alkoxy group may have from 1 to 6 or more carbon atoms or aryl; the process comprising reacting a compound of formula VII:

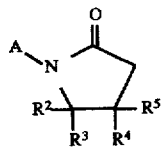

VII wherein $R^2$, $R^3$, $R^4$, $R^5$ and A are as defined for formulae IIa and IIb; with a base at a temperature from −100° to 10° C. followed by a sterically hindered chiral oxidising agent.

7. A process as claimed in claim 6, which gives an enantiomeric excess of the required isomer of at least 10%, enantiomeric excess being defined as:

$$\frac{(\% \text{ major enantiomer}) - (\% \text{ minor enantiomer})}{(\% \text{ major enantiomer}) + (\% \text{ minor enantiomer})}$$

8. A process as claimed in claim 6, wherein the base is a strong base such as lithium hexamethyldisilazide.

9. A process as claimed in claim 6, wherein the sterically hindered chiral oxidising agent is (+) or (−)camphoryl sulfonyl oxaziridine.

10. A process for the preparation of a compound of formula Ia or Ib:

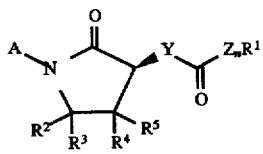

Ia

-continued

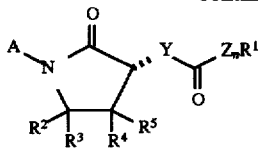

Ib wherein $R^2$, $R^3$, $R^4$, $R^5$ and A are as defined for formulae IIa and IIb;

Z is O, S or $NR^6$;
n is 0 or 1;
Y is O, S or $NR^7$;
$R^6$ is hydrogen or $C_1$–$C_4$ alkyl;
$R^7$ is H, OH, CHO or $NR^{17}R^{18}$, or $C_1$–$C_{10}$ hydrocarbyl or $O(C_1$–$C_{10}$ hydrocarbyl) either of which may be substituted with up to two substituents chosen from $OR^{17}$, $COR^{17}$, $COOR^{17}$, $OCOR^{17}$, CN, halogen, $S(O)_pR^{17}$, $NR^{17}R^{18}$, $NO_2$, $NR^{17}COR^{18}$, $NR^{17}CONR^{18}R^{19}$, $CONR^{17}R^{18}$ and heterocyclyl;
$R^{17}$, $R^{18}$ and $R^{19}$ independently represent hydrogen, $C_1$–$C_6$ hydrocarbyl or $C_1$–$C_6$ halohydrocarbyl;
p is 0, 1 or 2;
alternatively;
when Y is $NR^7$ and either Z is $NR^6$ or n is 0, $R^7$ and the substituents of Z or $R^1$ may together form a bridge represented by the formula $-Q^1-Q^2-$ or $-Q^1-Q^2-Q^3-$, where $Q^1$, $Q^2$ and $Q^3$ independently represent $CR^{13}R^{14}$, $=CR^{13}$, CO, $NR^{16}$, $=N$, O or S;

$R^{13}$ and $R^{14}$ independently represent hydrogen, $C_1$–$C_4$, alkyl, OH or halogen;

$R^{16}$ represents hydrogen or $C_1$–$C_4$ alkyl;

$R^1$ is hydrogen, or $C_1$–$C_{10}$ hydrocarbyl or heterocyclyl having 3 to 8 ring atoms either of which may optionally be substituted with halogen, hydroxy, $SO_2NR^aR^b$ where $R^a$ and $R^b$ independently represent hydrogen or $C_1$–$C_6$ alkyl, $SiR^c_3$ where each $R^c$ is independently $C_1$–$C_4$ alkyl or phenyl, cyano, nitro, amino, mono- and dialkylamino in which the alkyl groups have from 1 to 6 or more carbon atoms, acylamino, $C_1$–$C_6$ alkoxy, $C_1$–$C_6$ haloalkoxy, $C_1$–$C_6$ alkylthio, $C_1$–$C_6$ alkylsulphinyl, $C_1$–$C_6$ alkylsulphonyl, carboxy, carboxyamide in which the groups attached to the N atom may be hydrogen or optionally sustituted $C_1$–$C_{10}$ hydrocarbyl, alkoxycarbonyl wherein the alkoxy group may have from 1 to 6 or more carbon atoms or aryl;

the process comprising preparing a compound of formula IIa or IIb by a process as claimed in any one of claims 1, 4 or 6 and reacting the compound of formula IIa or IIb, or the corresponding compound in which the 3—OH group has been converted to a 3—SH or 3—$NHR^7$ group, wherein $R^7$ is as defined for formulae Ia and Ib, with a compound having one or more acyl groups.

* * * * *